(12) United States Patent
Meyer et al.

(10) Patent No.: US 7,699,794 B2
(45) Date of Patent: Apr. 20, 2010

(54) MASSAGER WITH SHOCK ABSORPTION, MULTIPLE CONTACT SURFACES AND VISUAL THERAPY EFFECTS

(75) Inventors: Elizabeth Harrison Meyer, Birmingham, MI (US); Mordechai Lev, West Bloomfield, MI (US); Huang Wen Wei, Xiamen (CN)

(73) Assignee: fka Distributing Co., Commerce Township, MI (US)

( * ) Notice: Subject to any disclaimer, the term of this patent is extended or adjusted under 35 U.S.C. 154(b) by 776 days.

(21) Appl. No.: 11/083,593

(22) Filed: Mar. 18, 2005

(65) Prior Publication Data

US 2006/0211961 A1 Sep. 21, 2006

(51) Int. Cl.
*A61H 1/00* (2006.01)
(52) U.S. Cl. .......................................... 601/15; 601/46
(58) Field of Classification Search .................... 601/15, 601/70, 72, 137, 138, 46; 15/22.1, 22.2, 15/22.4
See application file for complete search history.

(56) References Cited

U.S. PATENT DOCUMENTS

| | | | |
|---|---|---|---|
| 1,301,866 A | 4/1919 | Moore | |
| 1,377,140 A | 5/1921 | North | |
| 2,466,659 A | 4/1949 | Korpela | |
| 2,523,547 A | 9/1950 | Zerkle | |
| 2,964,037 A | 12/1960 | Johnston | |
| 4,025,809 A | 5/1977 | Teranishi | |
| 4,149,530 A | 4/1979 | Gow | |
| 4,150,668 A | 4/1979 | Johnston | |
| 4,224,932 A | 9/1980 | Farb | |
| 4,604,993 A | 8/1986 | Moriwaki et al. | |
| 4,825,853 A | 5/1989 | Iwamoto et al. | |
| 4,958,628 A | 9/1990 | Iwamoto et al. | |
| 5,193,528 A | 3/1993 | Iwamoto et al. | |
| 5,471,695 A * | 12/1995 | Aiyar | 15/22.1 |
| 5,716,332 A | 2/1998 | Noble | |
| 5,935,089 A | 8/1999 | Shimizu | |
| 5,997,489 A | 12/1999 | Iwamoto et al. | |
| 6,026,828 A * | 2/2000 | Altshuler | 132/311 |
| 6,135,561 A * | 10/2000 | Kruger et al. | 297/408 |
| 6,679,857 B1 | 1/2004 | Bastia et al. | |
| 6,711,823 B2 * | 3/2004 | Floessholzer | 30/216 |
| 2002/0169400 A1 | 11/2002 | Huang | |
| 2004/0147984 A1 * | 7/2004 | Altshuler et al. | 607/88 |
| 2005/0159687 A1 | 7/2005 | Mizuuchi | |
| 2005/0187597 A1 | 8/2005 | Vanderschuit | |
| 2005/0209539 A1 | 9/2005 | Lev et al. | |

FOREIGN PATENT DOCUMENTS

EP 0 001 833 A2 5/1979

* cited by examiner

*Primary Examiner*—Michael A. Brown
(74) *Attorney, Agent, or Firm*—Brooks Kushman P.C.

(57) ABSTRACT

A handheld massager is disclosed having a spring and dampener provided between a massage head portion and a handle portion of a massager. A massage mechanism is provided in the massage head portion for application of a massage effect to the user. Resulting shock and vibrations caused by the massage effect are absorbed and dampened by the spring and dampener for minimizing these effects upon the hand and wrist of the user. Additionally, variable vibrational contact surfaces and various visual therapy effects are disclosed in combination with the massage effect.

20 Claims, 4 Drawing Sheets

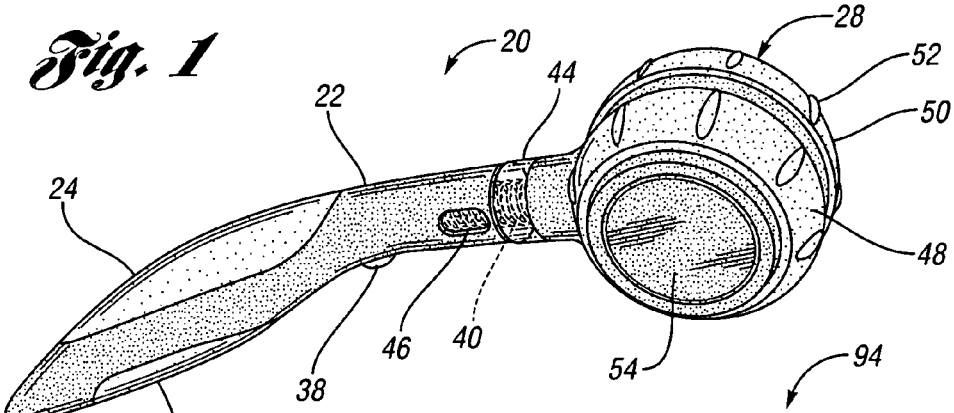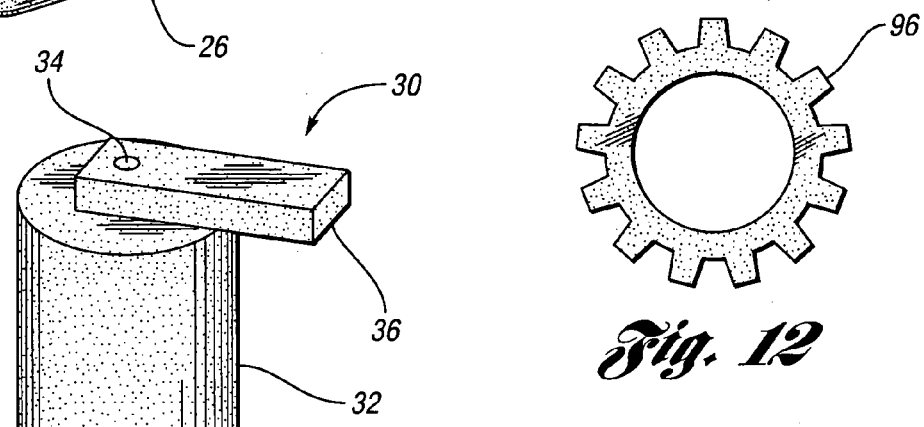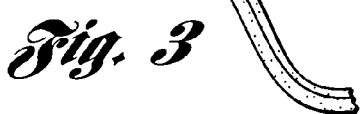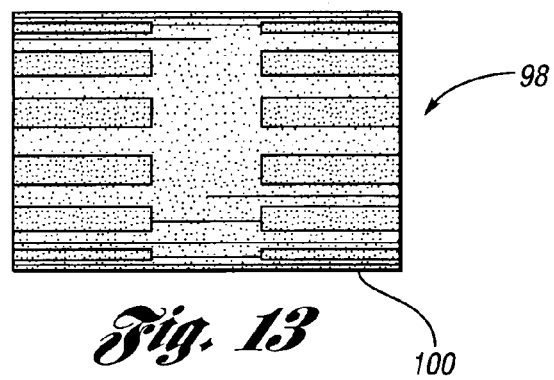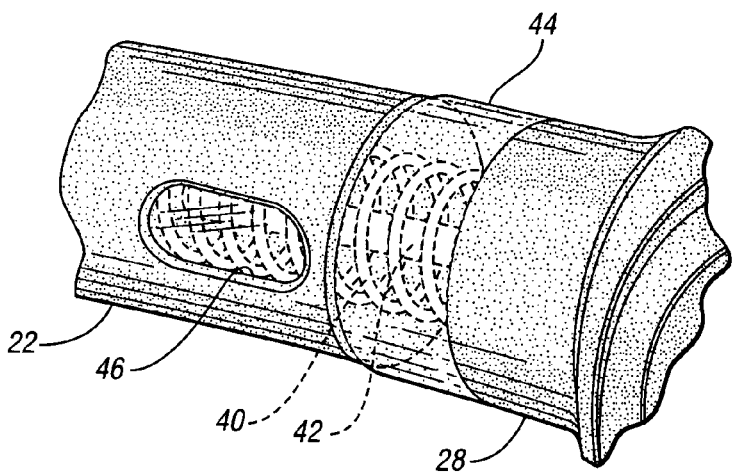

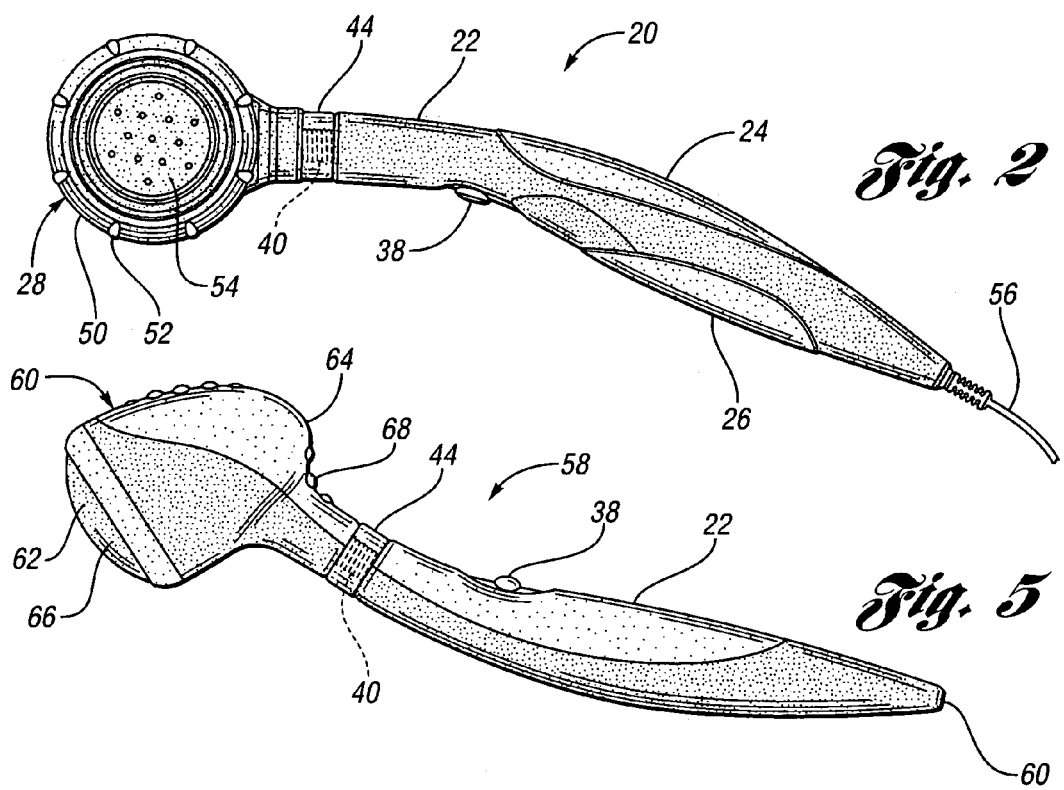
Fig. 2
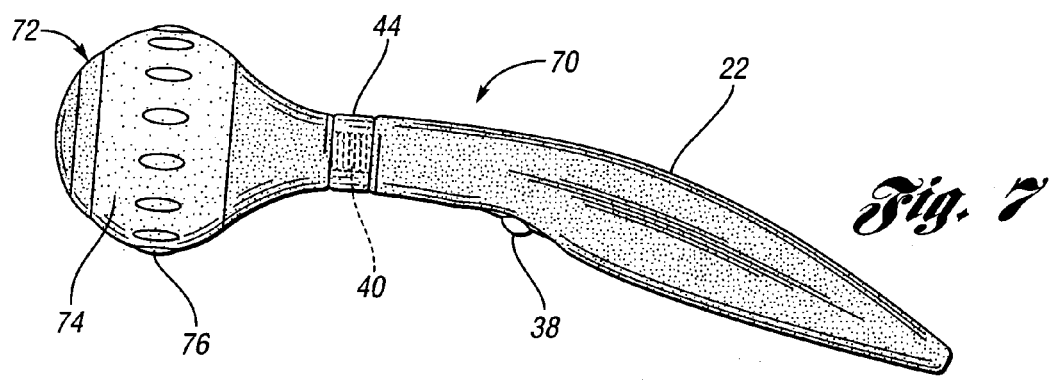
Fig. 5
Fig. 7
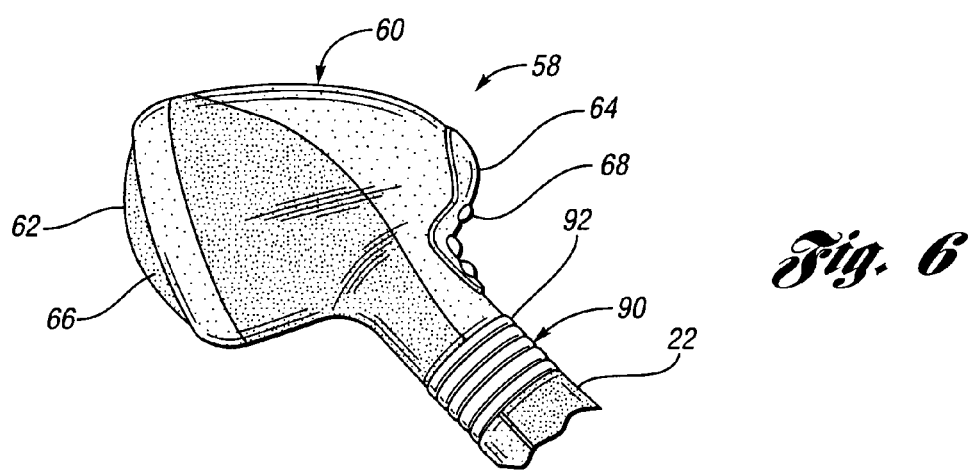
Fig. 6

MASSAGER WITH SHOCK ABSORPTION, MULTIPLE CONTACT SURFACES AND VISUAL THERAPY EFFECTS

BACKGROUND OF THE INVENTION

1. Field of the Invention

The present invention relates to massagers, more particularly to power-operated massagers.

2. Background Art

Power-operated massagers are often used to treat muscle tension and fatigue. Power-operated massagers may provide a vibrating massage effect, a percussive massage effect, a kneading massage effect, a rubbing massage effect, a rolling massage effect, a Shiatsu massage effect, or the like.

Often, these massage effects are provided in power operated massagers that are adapted for handheld operation. Thus, many of these massagers are embodied in an apparatus having a handle to be grasped and manipulated by the user. Due to the massage effect of a particular massager, resultant vibrations from the massage effect are often imparted to the massager, which are translated through the handle portion to the hand and wrist of the user.

Oftentimes, the massage feature of a massager is provided spaced away from the handle portion so that the user may apply the massage to a body part. The length of the handle portion may magnify the resultant moment or torque experienced by the user.

Handheld massagers are often limited in visual therapeutic effects.

Handheld vibratory massagers are often limited in features of versatility.

A goal of the present invention is to reduce shock and vibrations imparted to the hand of the user when operating a handheld massager. Another goal of the present invention is to improve visual therapeutic effects of a handheld massager. A further goal of the present invention is to improve the effectiveness and versatility of handheld vibratory massagers.

SUMMARY OF THE INVENTION

An aspect of the present invention is to provide a handheld massager having an elongate handle portion and a massage head portion. The massage head portion is mounted to a spring on the handle portion and a dampener is oriented between the handle and massage head portion. A massage mechanism is mounted in the massage head for imparting a massage effect. The spring and dampener collectively absorb and dampen the massage effect imparted from the massage head portion to the handle portion.

A further aspect of the present invention is wherein the dampener is transparent.

Another aspect of the present invention is wherein a fluid is disposed within the dampener for even distribution of vibration through the dampener.

Another aspect of the present invention is to provide ribs in the dampener for facilitating deformation of the dampener while absorbing the massage effect.

An aspect of the prevent invention is to provide a handheld massager having a handle portion and massage head portion. A motor is oriented in the massage head portion for driving an eccentric weight thereby generating a vibratory massage effect. Ornamental indicia is mounted to the massage head portion and a partial window is mounted to the massage head portion. The window is displaced over the indicia for providing a partial view of the indicia. One of the indicia or partial window is driven by the motor for displaying a visual rotary effect in combination with the vibratory massage effect.

Another aspect of the present invention is to provide a massager having an elongate arcuate handle portion with a massage head portion pivotally connected thereto. A vibratory massage mechanism is provided within the massage head portion. The user may pivot the massage head portion for a desired orientation for applying the massage effect from one of a plurality of massage contact portions provided about the massage head portion.

The above aspects, and other aspects, objects, features, advantages, embodiments and benefits of the present invention are readily apparent from the detailed description of the embodiments of the invention when taken in connection with the accompanying drawings.

BRIEF DESCRIPTION OF THE DRAWINGS

FIG. 1 is a perspective view of a handheld massager in accordance with the present invention;

FIG. 2 is a side elevation view of the massager in FIG. 1;

FIG. 3 is a perspective view of a massage mechanism for the massager in FIG. 1;

FIG. 4 is an enlarged partial perspective view of a dampener of the massager in FIG. 1;

FIG. 5 is a side elevation view of an alternative embodiment handheld massager in accordance with the present invention;

FIG. 6 is an enlarged side elevation view of a massage head portion of the massager of FIG. 5;

FIG. 7 is a side elevation view of another alternative embodiment handheld massager in accordance with the present invention;

FIG. 12 is an axial end view of an alternative embodiment dampener in accordance with the present invention;

FIG. 13 is a side elevation view of another alternative embodiment dampener in accordance with the present invention.

DETAILED DESCRIPTION OF EMBODIMENTS OF THE INVENTION

Figure 8:
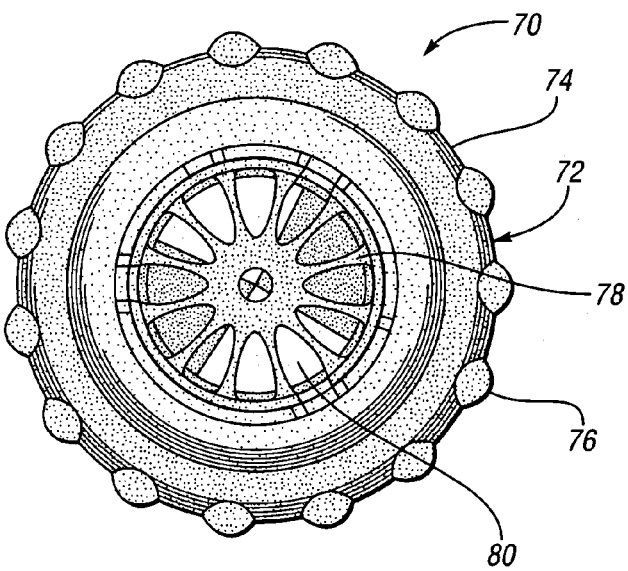
FIG. 8 is a top plan view of the massager of FIG. 7.

With reference now to FIGS. 1 and 2, an exemplary embodiment handheld massager 20 is illustrated in accordance with the present invention. The handheld massager 20 includes an elongate handle portion 22 that is formed as a two-piece housing from a high strength polymer for being both lightweight and structurally sound. The handle portion 22 includes a pair of elastomeric grip pads 24, 26 for providing a padded and comfortable grip to a user and for enhancing the grasp of the user thereabout. The handle portion 22 is generally arcuate for facilitating the application of a massage effect to a body part of the user. The curved shape of the handle portion 22 assists the user, for example, in reaching the user's back. Prior art massagers that are generally linear in shape may provide interference with the user's shoulders or other body parts and may result in an indirect application of the massage effect.

The massager 20 includes a massage head portion 28 mounted to the handle portion 22. The massage head portion 28 includes a massage mechanism mounted therein for imparting the massage effect. With reference now to FIG. 3, the massage mechanism is illustrated as a vibratory massage mechanism 30. The vibratory massage mechanism 30 includes a motor 32 having a rotary output shaft 34. An eccentric weight 36 is mounted upon the rotary output shaft 34 so as the motor drives the eccentric weight 36, the eccentric weight 36 imparts a vibratory massage effect to the vibratory massage mechanism 30 and the massage head portion 28. The vibratory massage mechanism 30 is mounted generally coaxial with the connection of the massage head portion 28 with the handle portion 22 so that the vibratory massage effect is imparted in a plane that is generally perpendicular to the connection.

The handle grip portion includes a power switch 38 located proximate to the grip pads 24, 26 so that the user may control the operation of the motor 32.

Referring now to FIG. 4, an enlarged view of the connection between the handle portion 22 and the massage head portion 28 is illustrated. Specifically, a coil spring 40 is mounted within a distal end of the handle portion 22 and extends longitudinally therefrom. The massage head portion 28 is mounted to coil spring 40. Thus, a flexible, yet secure connection is provided between the handle portion 22 and the massage head portion 28. Since the coil spring 40 is generally hollow, it acts as a conduit for wiring 42 that extends from the handle portion 22 to the massage head portion 28. Of course, the invention contemplates other biasing members such as leafsprings or the like.

Prior art vibratory massagers often include a spring between the handle portion 22 and the massage head portion 28. Springs alone are not sufficient for absorbing shock at this connection because springs generally absorb a force and consequently return a resultant force in an opposite direction. Accordingly, a dampener 44 is provided between handle portion 22 and the massage head portion 28 for dampening vibrations therethrough. The spring 40 and the dampener 44 collectively absorb and dampen shock and vibrations imparted from the massage head portion 28 to the handle portion 22.

The spring 40 and the dampener 44 are aligned coaxially for uniform cooperation at the connection. As illustrated, the spring 40 may be disposed within the dampener 44. The dampener 44 as illustrated in FIG. 4 is a solid elastomeric shroud having a sufficient wall thickness for absorbing vibrations therethrough. Additionally, the dampener 44 is transparent for enhancing a visual effect of the connection. For example, the user may view the spring 40 and wiring 42 through the dampener 44. Additionally, a light source (not shown) such as light emitting diodes (LED's) are provided within the handle portion 22 for illuminating the dampener 44 during operation. For example, blue LED's are provided at an axial end of the dampener 44 within the handle portion 22 for illuminating the dampener 44 blue in color during operation.

The view of the spring 40 and dampener 44 can be extended by a window 46 formed in the handle portion 22. Accordingly, a recess is formed in the distal end of the handle portion 22 for receiving a portion of the spring 40 and the dampener 44 therein. Likewise a recess may also be formed within the massage head portion 28.

The invention contemplates varying dampeners with varying material characteristics. For example, the dampener 44 may contain a fluid therein such as a gel for providing a uniform hoop stress to the shroud as a result of shock and vibrations imparted thereto.

Referring again to FIGS. 1 and 2, the massage head portion 28 may be provided with a pair of rollers 48, 50 so that the massage head, portion 28 may be rolled along the body part, thereby reducing friction therebetween while providing a rolling massage effect. The rollers 48, 50 each include a series of treads 52 formed thereabout for providing vibratory massage nodes during the vibratory massage operation and for providing traction for the rollers 48, 50.

The massage head portion 28 also includes at least one heat therapy pad 54 provided on a lateral side thereof for providing a heated therapeutic effect to the body part of the user. The heated therapy pad 54 may be an infrared pad for conveying infrared rays. Infrared rays allow heat to penetrate deep underneath the surface of the skin, causing the pores of the skin to be opened and promoting metabolism and excretion of the body to increase blood circulation. The operation of heat therapy pad 54 may be controlled by the power switch 38 and may be operated alone or in combination with the vibratory massage mechanism 30.

Red LED's may also be provided in the handle portion 22 rearward of the recess for illuminating the dampener 44 red in color when the heat therapy pad 54 is in operation. The operation of the handheld massager 20 is powered via a conventional power cord 56. A transformer may be provided within the massage unit 20 for converting the power from AC to DC.

With reference now to FIG. 5, an alternative embodiment handheld massager 58 is illustrated in accordance with the present invention. Unlike the prior embodiment, the massager 58 is not corded, rather the massager 58 includes a receptacle 59 for receiving a power sources for charging a rechargeable battery provided with the handle portion 22. The massager 58 includes green and yellow LED's within the handle portion 22 for imparting various illumination effects to the dampener 44. The green LED's are illuminated in ordinary operation of the massager 58; and the yellow LED's are illuminated to indicate when the rechargeable battery needs to be recharged.

The massager 58 includes a massage head portion 60 having various contact formations provided thereon. Referring now to FIG. 6, the massage head portion 60 includes an enlarged dome shaped massage contact surface 62 and a spaced apart elastomeric massage node 64. The massage head portion 60 includes a vibratory massage mechanism such as the vibratory massage mechanism 30 in FIG. 3 for imparting a vibratory massage effect to the contact surface 62 and the message node 64. Similar to the prior embodiment, the vibratory massage mechanism is oriented generally co-linear with the dampener 44 and the spring 40 for imparting the vibratory massage effect in a plane that is generally perpendicular to the handle portion 22.

The massage head portion 60 is pivotally connected to the handle portion 22 so that a desired orientation of the massage head portion 60 may be selected relative to the handle portion 22 for applying one of the contact surface 62 or the massage node 64 against the targeted area.

The massage contact surface 62 includes a heat therapy pad 66 thereon for providing a heated therapeutic effect in combination with the vibratory massage effect. The massage node 64 is provided at a peak of the massage head portion 60 and may be utilized for targeting specific areas of the body, such as an upper region of a back, neck muscles, or the like. A series of secondary massage nodes 68 are provided adjacent to the massage node 64 for imparting the vibratory massage effect to a body part adjacent to that targeted by the primary massage node 64.

With reference now to FIG. 7, another alternative embodiment handheld massager 70 is illustrated in accordance with the present invention. The massager 70 is also a rechargeable massager having a handle portion 22 connected to a massage head portion 72 via a spring 40 and a dampener 44. The massage head portion 72 includes a vibratory massage mechanism such as the mechanism 30 illustrated in FIG. 3. The massage mechanism is also oriented generally coaxial with the spring 40 and the dampener 44 at the connection of the massage head portion 72 to the handle portion 22. The massage head portion 72 includes a roller 74 provided thereabout generally coaxial with the handle portion 22 for providing a rolling vibratory massage effect that may be useful for a user to move the massage head portion 72 transversely across a body part, rather than longitudinally as provided in the massager 20 of FIGS. 1 and 2. The roller 74 includes a series of treads 76 formed about its periphery for acting as vibratory massage nodes during the vibratory massage effect and for enhancing traction between the roller 74 and the body part of the user.

The massager 70 provides a therapeutic visual effect in combination with the vibratory massage effect. With reference now to FIG. 8, the massage head portion 72 includes a partial window 78 on an axial end thereof for view therethrough. Ornamental indica 80 is provided beneath the window 78. The indica 80 is driven by the motor 32 of the vibratory massage mechanism 30 so that as the vibratory massage effect is imparted to the massage head 72, a therapeutic visual effect is provided through the window 78 by the rotation of the indicia 80. Thus, the user may be soothed and relaxed by both the massage effect and the visual effect of the massager 70.

Figures 9, 10:
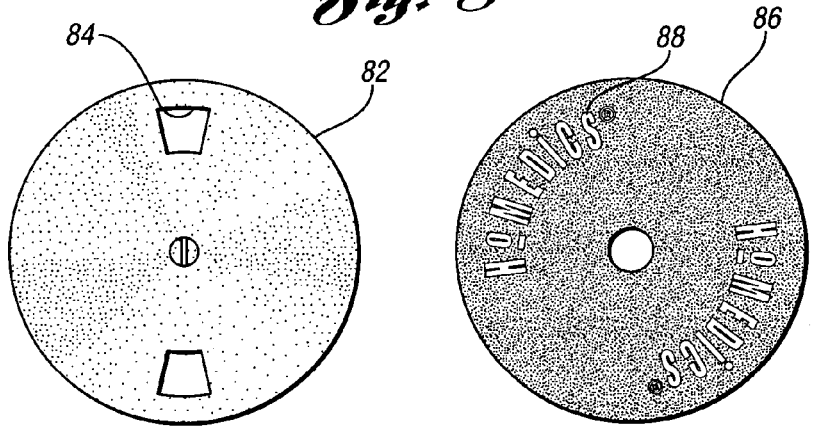
FIG. 9 is a top plan view of an alternative embodiment window for the massager of FIG. 7.
FIG. 10 is a top plan view of alternative embodiment indicia for the massager of FIG. 7.
Figure 11:
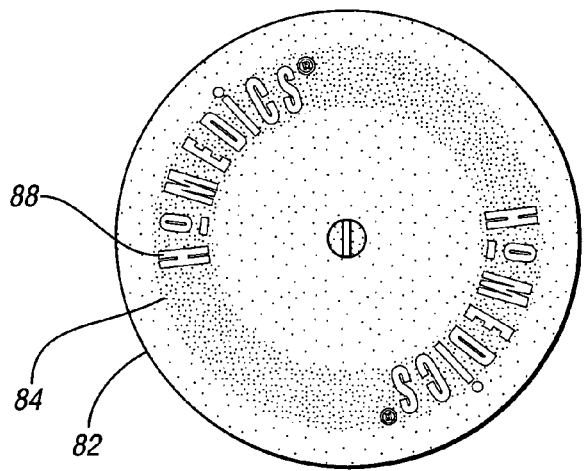
FIG. 11 is a top plan view of the window of FIG. 9 and the indicia of FIG. 10, illustrated in operation of the massager.

Alternatively, a subtle visual effect may be provided which may convey text. Referring now to FIGS. 9 through 11, an alternative embodiment visual effect is provided by a window disc 82 having partial window apertures 84 formed at radial positions of the disc 82. An ornamental disc 86 may be provided beneath the window disc 82. The ornamental disc 86 may include indicia thereon or a logo 88 bearing a message or manufacturer mark. When the massager 70 is not in operation, only a partial portion of the logo is viewable through the window apertures 84. The window disc 82 is driven by the vibratory massage mechanism 30 such that during operation of the massage effect of the massager 70, the window disc 82 is rotated and the logo 88 is viewable through the apertures 84 thereby providing a subtle display of the logo as illustrated in FIG. 11.

In the stopped orientation of the window disc 82, the window apertures 84 may stop at text that states "Revive," if the rechargeable battery requires recharging.

Referring again to FIG. 6, an alternative embodiment dampener 90 is illustrated having a series of transverse ribs 92. Solid dampeners may be too rigid for some applications. The ribs 92 provide accordion-style flexibility for the dampener 90 so that an optimal amount of shock absorption and flexibility is provided between the handle portion 22 and the massage head portion 60. Thus, greater deformation is permitted by the dampener 90 than the solid dampener 44 illustrated in FIG. 5 so that the proper tradeoff of flexibility and shock absorption is provided from the massage head portion 60 the handle portion 22.

Various rib configurations are contemplated by the present invention. For example, with reference to FIG. 12, another alternative embodiment dampener 94 is illustrated having a plurality of ribs 96 formed longitudinally thereabout for permitting a predetermined amount of deformation of the dampener 94 while absorbing vibrations conveyed thereto.

The invention contemplates that the dampener 94 may be provided with ribs 96 without interfering with a visual effect provided to the body of the dampener 94. With reference now to FIG. 13, another alternative embodiment dampener 98 is illustrated having a plurality of longitudinal ribs 100 formed within a partial length at opposed distal ends of the dampener 98. Each of the ribbed ends of the dampener 98 are provided within a corresponding recess formed within each of the handle portion 22 and massage head portion 60, so that the ribs 100 do not obfuscate a visual therapeutic effect provided by the dampener 98. The invention also contemplates that the partial ribs 100 may be formed transversely.

Figure 14:
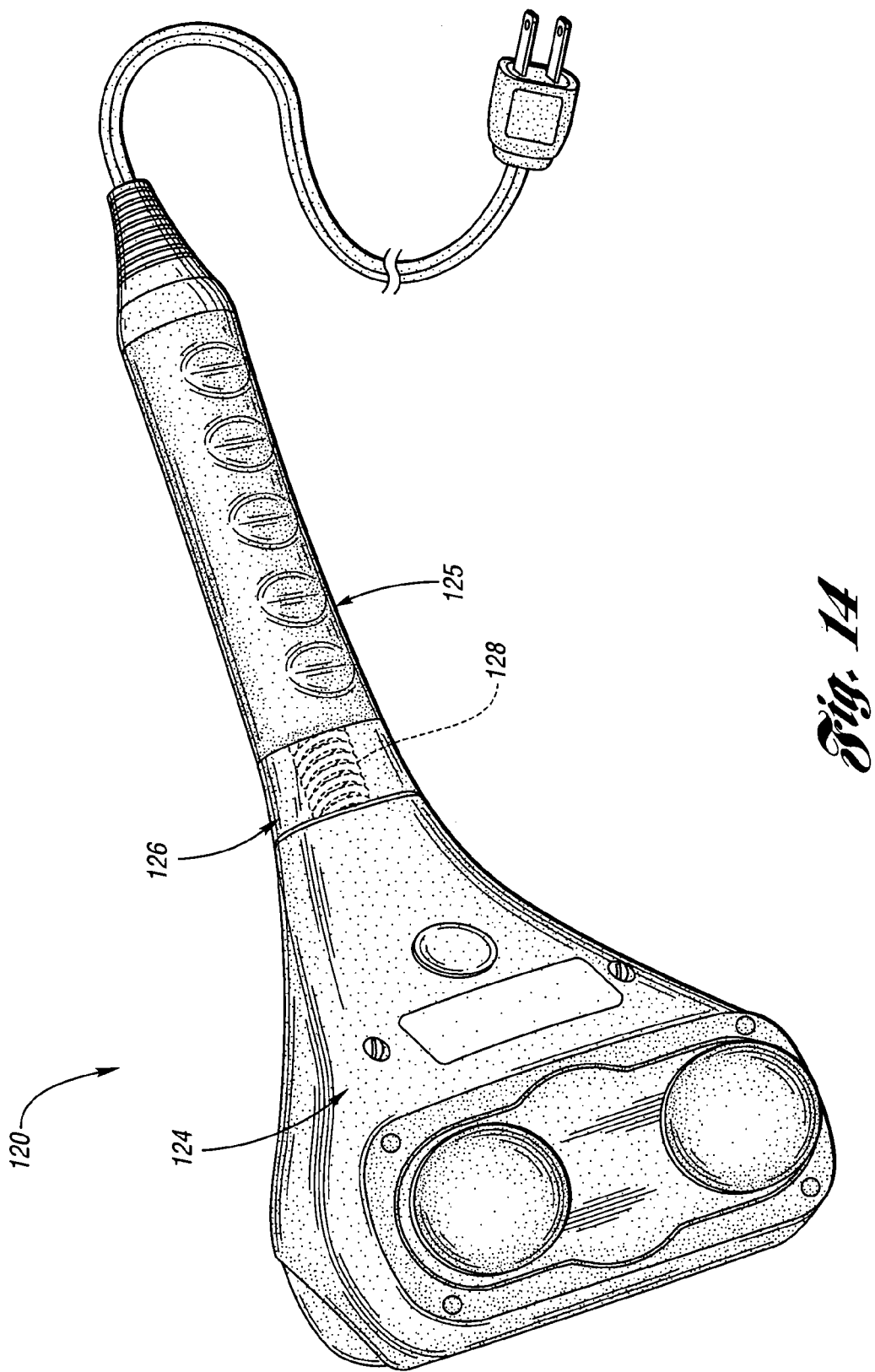
FIG. 14 is a perspective view of an alternative embodiment handheld massager in accordance with the present invention.

In FIG. 14, an alternative embodiment handheld massager 120 is illustrated in accordance with the present invention. Unlike the prior embodiment vibratory massagers, the massager 120 in FIG. 14 is a percussive massager, which is utilized for providing a percussive massage effect to a body part of the user. Percussive massagers are known in the art, such as the embodiments disclosed in U.S. patent application Ser. No. 10/495,738 filed on May 17, 2004 titled Percussive Massager With Variable Node Spacing, which is incorporated in its entirety by reference herein.

The percussive massager 120 includes a massage head portion 124 connected to handle portion 125 through a dampener 126 and a coil spring 128. Thus, as a percussive massage effect is imparted to a body part of the user, shock and vibrations that are experienced by the massage head portion 124 as a result of the percussive massage effect are absorbed and dampened by the dampener 126 and the spring 128 for minimizing the shock and vibration imparted to the hand and wrist of the user.

In summary, the present invention discloses improved characteristics of shock absorption, variable vibrational massage effects, and visual therapeutic effects to be utilized in combination with a handheld massager.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A handheld massager comprising:
   an elongate handle portion sized to be gripped by a user;
   a spring mounted to a first distal end of the handle portion;
   a massage head portion mounted to the spring;
   a dampener oriented between the handle portion first distal end and the massage head portion; and
   a massage mechanism oriented within the massage head portion for imparting a massage effect to the massage head portion;
   wherein the user may grasp the handle portion and apply the massage effect to a body part, and the spring and dampener collectively absorb and dampen the massage effect imparted from the massage head portion to the handle portion; and
   wherein the dampener is at least partially transparent and one of the handle portion and massage head portion further comprise a light source for illuminating the dampener.

2. The massager of claim 1 wherein the handle portion is generally arcuate for facilitating application of the massage head portion to the body part.

3. A handheld massager comprising:
   an elongate handle portion sized to be gripped by a user;
   a spring mounted to a first distal end of the handle portion;
   a massage head portion mounted to the spring;

a dampener oriented between the handle portion first distal end and the massage head portion; and a massage mechanism oriented within the massage head portion for imparting a massage effect to the massage head portion;

wherein the user may grasp the handle portion and apply the massage effect to a body part, and the spring and dampener collectively absorb and dampen the massage effect imparted from the massage head portion to the handle portion; and wherein the massage head portion further comprises a roller rotatably mounted thereto for rolling the massage head portion along the body part.

4. The massager of claim 3 wherein the handle portion is generally arcuate for facilitating application of the massage head portion to the body part.

5. A handheld massager comprising:
an elongate handle portion sized to be gripped by a user;
a spring mounted to a first distal end of the handle portion;
a massage head portion mounted to the spring;
a dampener oriented between the handle portion first distal end and the massage head portion; and
a massage mechanism oriented within the massage head portion for imparting a massage effect to the massage head portion;
wherein the user may grasp the handle portion and apply the massage effect to a body part, and the spring and dampener collectively absorb and dampen the massage effect imparted from the massage head portion to the handle portion; and
wherein the massage head portion further comprises a heater for imparting a heat therapy effect to the body part.

6. The massager of claim 5 wherein the handle portion is generally arcuate for facilitating application of the massage head portion to the body part.

7. The massager of claim 5 wherein the massage mechanism further comprises an eccentric weight driven by a motor for imparting a vibratory massage effect to the massage head portion.

8. A handheld massager comprising:
an elongate handle portion sized to be gripped by a user;
a spring mounted to a first distal end of the handle portion;
a massage head portion mounted to the spring;
a dampener oriented between the handle portion first distal end and the massage head portion; and
a massage mechanism oriented within the massage head portion for imparting a massage effect to the massage head portion;
wherein the user may grasp the handle portion and apply the massage effect to a body part, and the spring and dampener collectively absorb and dampen the massage effect imparted from the massage head portion to the handle portion;
wherein the dampener is hollow and the spring is disposed within the dampener; and
wherein the dampener is at least partially transparent so that a user may view the spring.

9. The massager of claim 8 wherein the massage mechanism further comprises a percussive massage mechanism.

10. The massager of claim 8 wherein the massage mechanism further comprises an eccentric weight driven by a motor for imparting a vibratory massage effect to the massage head portion.

11. The massager of claim 8 wherein the spring is further defined as a coil spring.

12. The massager of claim 8 wherein the handle portion is generally arcuate for facilitating application of the massage head portion to the body part.

13. A handheld massager comprising:
an elongate handle portion sized to be gripped by a user;
a spring mounted to a first distal end of the handle portion;
a massage head portion mounted to the spring;
a dampener oriented between the handle portion first distal end and the massage head portion; and
a massage mechanism oriented within the massage head portion for imparting a massage effect to the massage head portion;
wherein the user may grasp the handle portion and apply the massage effect to a body part, and the spring and dampener collectively absorb and dampen the massage effect imparted from the massage head portion to the handle portion; and
wherein the dampener is further defined as an elastomeric shroud.

14. The massager of claim 13 wherein the dampener further comprises a fluid disposed therein for even distribution of vibration.

15. The massager of claim 13 wherein the handle portion is generally arcuate for facilitating application of the massage head portion to the body part.

16. The massager of claim 13 wherein the massage mechanism further comprises a percussive massage mechanism.

17. The massager of claim 13 wherein the massage mechanism further comprises an eccentric weight driven by a motor for imparting a vibratory massage effect to the massage head portion.

18. A handheld massager comprising:
an elongate handle portion sized to be gripped by a user;
a spring mounted to a first distal end of the handle portion;
a massage head portion mounted to the spring;
a dampener oriented between the handle portion first distal end and the massage head portion; and
a massage mechanism oriented within the massage head portion for imparting a massage effect to the massage head portion;
wherein the user may grasp the handle portion and apply the massage effect to a body part, and the spring and dampener collectively absorb and dampen the massage effect imparted from the massage head portion to the handle portion;
wherein the dampener includes ribs formed therein for facilitating deformation of the dampener while absorbing the massage effect; and
wherein the ribs are oriented longitudinally.

19. The massager of claim 18 wherein one of the handle portion and the massage head portion includes a recess formed therein for partially receiving the dampener, and the ribs are formed within a region of the dampener that is enclosed within the recess.

20. A handheld massager comprising:
an elongate handle portion sized to be gripped by a user;
a spring mounted to a first distal end of the handle portion;
a massage head portion mounted to the spring;
a dampener oriented between the handle portion first distal end and the massage head portion; and
a massage mechanism oriented within the massage head portion for imparting a massage effect to the massage head portion;
wherein the user may grasp the handle portion and apply the massage effect to a body part, and the spring and dampener collectively absorb and dampen the massage effect imparted from the massage head portion to the handle portion;

wherein the massage mechanism further comprises an eccentric weight driven by a motor for imparting a vibratory massage effect to the massage head portion; and wherein the massage mechanism is powered via wires from the handle portion, that are oriented within the coil spring.

* * * * *

UNITED STATES PATENT AND TRADEMARK OFFICE
CERTIFICATE OF CORRECTION

PATENT NO. : 7,699,794 B2  Page 1 of 1
APPLICATION NO. : 11/083593
DATED : April 20, 2010
INVENTOR(S) : Elizabeth Harrison Meyer et al.

It is certified that error appears in the above-identified patent and that said Letters Patent is hereby corrected as shown below:

In the drawings Fig. 5, should read:

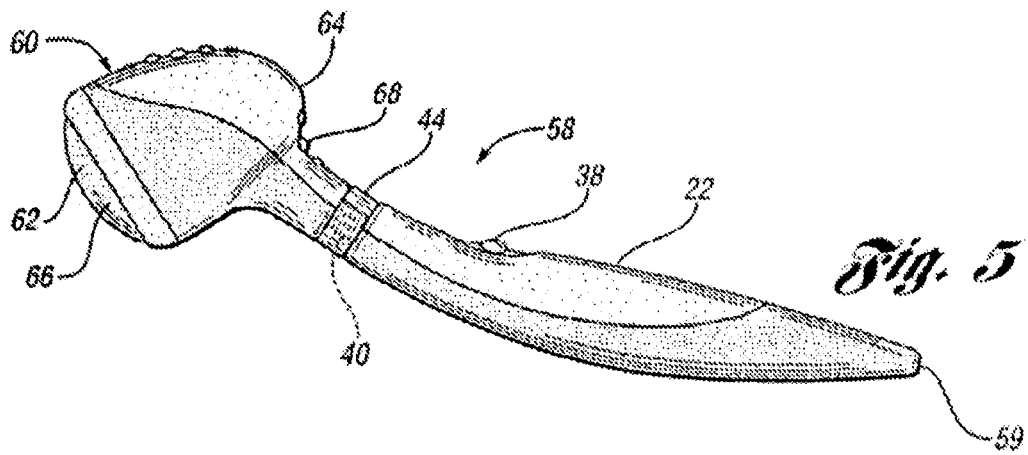

Signed and Sealed this

Seventeenth Day of August, 2010

David J. Kappos
*Director of the United States Patent and Trademark Office*